(12) United States Patent
Angermayer

(10) Patent No.: US 10,387,835 B2
(45) Date of Patent: Aug. 20, 2019

(54) VISUALLY REPRESENTING INFORMATION RELATED TO AN APPLICATION

(71) Applicant: SuccessFactors, Inc., South San Francisco, CA (US)

(72) Inventor: Thomas Angermayer, Sankt Leon—Rot (DE)

(73) Assignee: SuccessFactors, Inc., South San Francisco, CA (US)

( * ) Notice: Subject to any disclaimer, the term of this patent is extended or adjusted under 35 U.S.C. 154(b) by 875 days.

(21) Appl. No.: 14/953,510

(22) Filed: Nov. 30, 2015

(65) Prior Publication Data

US 2017/0154084 A1    Jun. 1, 2017

(51) Int. Cl.
```
G06F 16/00      (2019.01)
G06Q 10/10      (2012.01)
G06F 16/16      (2019.01)
G06F 16/18      (2019.01)
G06Q 50/24      (2012.01)
```

(52) U.S. Cl.
CPC ........... *G06Q 10/10* (2013.01); *G06F 16/168* (2019.01); *G06F 16/1873* (2019.01); *G06Q 50/24* (2013.01)

(58) Field of Classification Search
CPC ............ G06F 17/30563; G06F 16/168; G06F 16/1873
USPC ....................................................... 707/740
See application file for complete search history.

(56) References Cited

U.S. PATENT DOCUMENTS

```
5,806,078  A  *  9/1998  Hug .................. G06F 17/2288
                                                707/999.202
2001/0029517 A1* 10/2001 De Meno ............ G06F 11/1448
                                                        718/101
2005/0004816 A1*  1/2005 Abraham-Fuchs ... G06F 19/325
                                                          705/3
2015/0339282 A1* 11/2015 Goyal ................... G06F 17/241
                                                        715/229
```

* cited by examiner

*Primary Examiner* — Chelcie L Daye
(74) *Attorney, Agent, or Firm* — Fish & Richardson P.C.

(57) ABSTRACT

Various embodiments of systems, computer program products, and methods to visually represent information related to an application are described herein. A request can be received to view latest data modification information for an application. A plurality of data values and a plurality of data modification time periods corresponding to the plurality of data values can be retrieved. A plurality of latest data values from the retrieved plurality of data values can be visually modified. The modified data values and time periods can be displayed at the application.

20 Claims, 7 Drawing Sheets

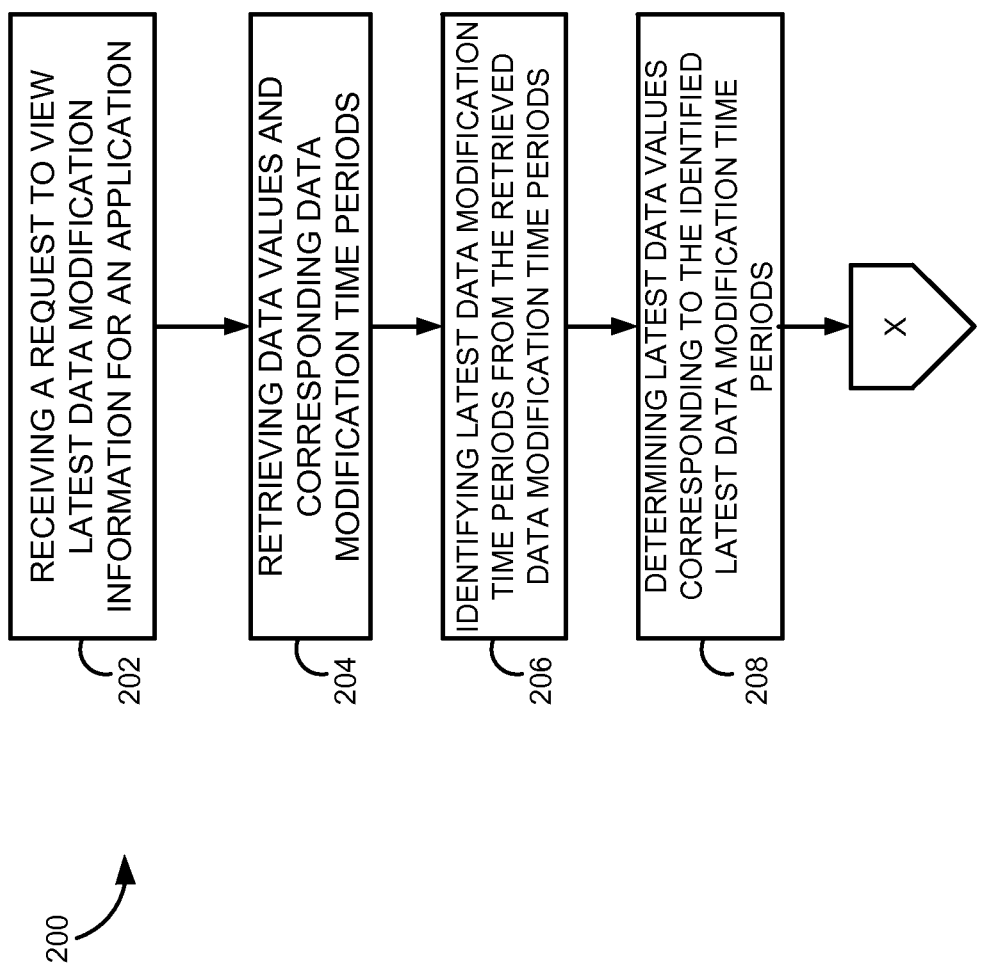

| Contact Information 402 | | |
|---|---|---|
| *Email Information* | | |
| *Email Type* | *Email Address* | *Is Primary* |
| Business 408 | *RevolutionUI@successfactors.com 420* | Yes 412 |
| | | |
| *Phone Information* | | |
| *Phone Type* | *Phone Number* | |
| Business 416 | +1-404-665-3421 410 | |
| | *+1-565-335-8989 428* | |
| | | |
| *Social Accounts Information* | | |
| *Domain* | *URL* | |
| *Yahoo Messenger 418* | *www.yahoo.com 422* | |
| AOL Instant Messenger 426 | *carla123 430* | |

| Data Modification Time Period 406 |
|---|
| 04/16/2015 ← 414 |
| 04/12/2015 ← 424 |
| 04/09/2015 ← 432 |

VISUALLY REPRESENTING INFORMATION RELATED TO AN APPLICATION

BACKGROUND

Present day applications are very interactive and allow users to enter values for the different fields of the application. Typically there may be several new or updated data values received for different fields of the application. A user may be interested to know about the different data values that were received earlier for the different fields of the application.

At present, applications provide a history option that allows user to view the previously received data values for the different fields of the application. When a user selects the history option then the user is shown the different data values arranged date-wise on a different page. In case a user wants to view previously received data value for a particular field, by selecting the history option, then the user has to view several non-relevant date-arranged pages till the user reaches the relevant page. Further the user also views previously received data values of other unrelated fields, which is undesirable.

SUMMARY

Methods and apparatus, including computer program products, are provided for visually representing information related to an application.

In one embodiment, a request to view latest data modification information for an application is received. A plurality of data values and a plurality of data modification time periods corresponding to the plurality of data values are then retrieved for a plurality of data fields of the application. Based on latest data modification time period from the plurality of time periods, a plurality of latest data values from the plurality of data values are visually modified. The plurality of latest data values include a data value, from the plurality of data values, received at the latest data modification time period. The visually modified plurality of data values are then displayed at the application.

The above methods, apparatus, and computer program products may, in some implementations, further include one or more of the following features.

The visually modifying the plurality of latest data values can include determining one or more data values from the plurality of latest data values that have same latest data modification time period; and visually modifying the determined one or more data values, wherein the one or more data values are identically modified.

The latest data modification time period can be visually modified. The latest modification time period and the plurality of latest data values can be identically modified.

A request to view previously received data values for a field of the application can be received. A plurality of previously received data values, corresponding to the field, from the plurality of data values can be retrieved. The retrieved plurality of previously received data values can be displayed at the application.

Receiving the request to view historical data can include detecting, a pointer on an area of the application including a latest data value corresponding to the field; and, based on the detecting, retrieving the previously received data values.

The plurality of data values can be received at the plurality of data modification time periods. The plurality of data values can be received at the application. The plurality of data values and the corresponding plurality of data modification time periods can be stored.

The latest data modification time period can be identified from the plurality of time periods. The plurality of latest data values can be determined from the plurality of data values corresponding to the identified latest data modification time period.

These and other benefits and features will be apparent upon consideration of the following detailed description of preferred embodiments thereof, presented in connection with the following drawings.

BRIEF DESCRIPTION OF THE DRAWINGS

The claims set forth the embodiments with particularity. The embodiments are illustrated by way of example and not by way of limitation in the figures of the accompanying drawings in which like references indicate similar elements. The embodiments, together with its advantages, may be best understood from the following detailed description taken in conjunction with the accompanying drawings.

FIGS. 2A-2B are different portions of a flow diagram illustrating a process to display the latest data values of an application, according to an embodiment.

FIG. 4 is a screenshot of an exemplary application including visually modified data values, according to an embodiment.

DETAILED DESCRIPTION

Embodiments of techniques for visually representing information related to an application are described herein. In the following description, numerous specific details are set forth to provide a thorough understanding of the embodiments. One skilled in the relevant art will recognize, however, that the embodiments can be practiced without one or more of the specific details, or with other methods, components, materials, etc. In other instances, well-known structures, materials, or operations are not shown or described in detail.

Reference throughout this specification to "one embodiment", "this embodiment" and similar phrases, means that a particular feature, structure, or characteristic described in connection with the embodiment is included in at least one embodiment. Thus, the appearances of these phrases in various places throughout this specification are not necessarily all referring to the same embodiment. Furthermore, the particular features, structures, or characteristics may be combined in any suitable manner in one or more embodiments.

Figure 1:
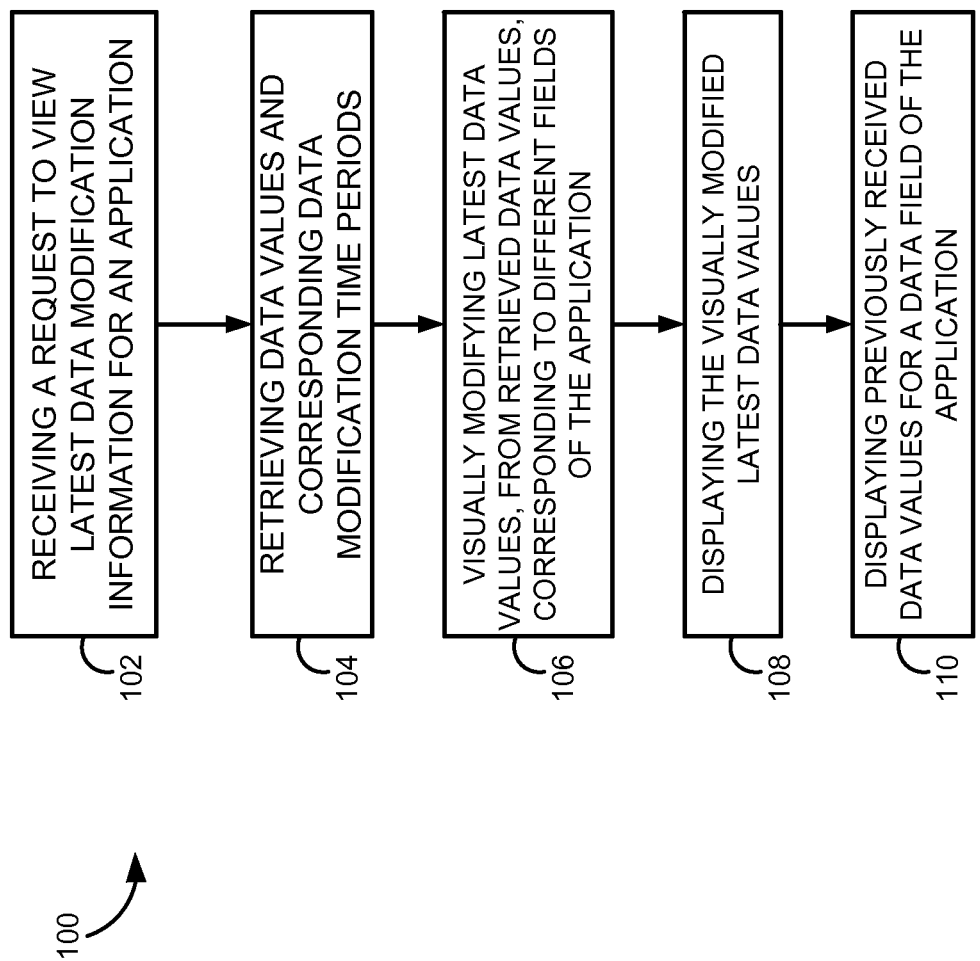
FIG. 1 is a flow diagram illustrating a process to visually represent application historical information, according to an embodiment.

FIG. 1 is a flow diagram 100 illustrating a process 100 to visually represent application historical information, according to an embodiment. An application software, or application, is a software program for performing a particular task. For example, the application may be an employee information management application for managing one or more employee records. An application may include several fields. In one embodiment, a field represents a particular group of data in an application. For example, a name field represents a group of names (data) in an application, and an address field represents a group of address (data) in the application. In one embodiment, the application may be executed on a portable electronic device. A portable electronic device may be cellular or satellite telephone, laptop computer, personal digital assistant, electronic book reader, wearable device such as smart watch, intelligent eyewear, etc. The application may be displayed on the user interface of the portable electronic device. The application may receive input either via an input device including, for example, a keyboard or a mouse, or via physical interaction of the user with the user interface including, for example, a touchscreen.

At 102, a request is received to view the latest data modification information for an application. The latest data modification information may correspond to the most recent data modification information for an application. The request may be received from a user viewing the application on the user interface. The data modification information may include a new data value for a field of the application or a modification to an existing data value for a field of the application. The new data value or the modification to an existing data value may be received at a data modification time period. In one embodiment, a data modification time period indicates a time when a new data value or a modification to an existing data value is received at the application. The data modification time period may be a date when the new data value or modification to data value is received or a more detailed time period including, for example, hours, minutes, and seconds of the particular date when the new data value or modification to data value is received.

In one embodiment, the latest data modification information may be the latest (i.e., the most recent) data values, which may be a new data value or a modification to an existing data value, corresponding to different fields of the application. The latest data values may be received at a corresponding latest data modification time periods. The latest data modification time period is a time when the last data modification corresponding to different fields of the application are received. For example, when a data value "U.S.A" and a data value "Germany" is received for a data field "Country" on "10 Oct., 2015" and "11 Oct., 2015", respectively, then the latest data value for the "Country" field is the last received data value "Germany".

At 104, data values and corresponding data modification time periods are retrieved. The data values received for the different fields of the application may be stored along with the corresponding data modification time periods. For example, a hospital record application that maintains health records of different patients may have two fields "name" and "medical condition" that has corresponding patient name data values and medical condition data values. Table 1 shows the values received for the name and medical condition fields of the hospital record application and the corresponding data modification time period when these data values are received.

TABLE 1

| Name | Medical Condition | Data Modification Time Period |
|---|---|---|
|  | Normal | 30 Oct., 2015 |
| John | Critical | 21 Oct., 2015 |
| Jotn |  | 11 Oct., 2015 |

In this case the data values for the "Name" data field "Jotn" and "John" are retrieved along with the corresponding data modification time period "11 Oct., 2015" and "21 Oct., 2015", respectively, when these data values are received at the application. Similarly the "Normal" and "Critical" data values for the "Medical Condition" field are retrieved along with the corresponding data modification time periods "30 Oct., 2015" and "21 Oct., 2015", respectively.

At 106, the latest data values retrieved from the plurality of data values corresponding to different fields of the application are visually modified. In one embodiment, visual modification is a process of modifying the visual appearance of an object. Visual appearance may include one or more of a color, a font size, a background, or any other property of the object that may be visualized. In one embodiment, the latest data values of the application, from the plurality of retrieved data values of the application, are identified and these latest data values are then visually modified. The latest data values may be identified corresponding to the different data fields of the application. In one embodiment, the latest time period when the last data value for a particular data field is determined and then the latest data value corresponding to the latest time period is identified. In one embodiment, the latest data value is also visually modified. The visually modified latest data values are then displayed at the application at 108.

For the hospital record application example shown in Table 1, two data values "Jotn" and "John" are received for the field "Name" on 11 Oct., 2015 and 21 Oct., 2015, respectively. Based on the received data values of the "Name" and the corresponding data modification time periods, the latest received data value for the "Name" field is "John" because "John" is received at the latest time period (21 Oct., 2015). Similarly, "Normal" is identified as the latest data value corresponding to the "Medical Condition" field. The latest data values "John" and "Normal" may then be visually modified along with the corresponding time periods "21 Oct., 2015" and "30 Oct., 2015", respectively. For example, the data value "John" and time period "21 Oct., 2015" may be visually modified such that the font color of "John" and "21 Oct., 2015" is changed to orange, as represented by italicized text in Table 2. Similarly the data value "Normal" and the time period "30 Oct., 2015" may be visually modified such that the font color of "Normal" and "30 Oct., 2015" is changed to green, as represented by bold text in Table 2.

TABLE 2

| Name | Medical Condition | Data Modification Time Period |
|---|---|---|
|  | Normal | 30 Oct., 2015 |
| *John* |  | *21 Oct., 2015* |

At 110, previously received data values for a particular data field may then be displayed on the same application screen. Previously received data values may include data values that were received prior to receiving the latest data value for a particular data field. A user may request display of the previously received data values for a particular field. In one embodiment, the request to view previously received data values and the display of the previously received data values may be performed before receiving the request to view latest data modification information. For the hospital record application shown in Table 1, when a request is received to view historical data value for name field then the data value "Jotn" is displayed, for example.

In this way, a user may easily visualize, on the same application screen, the latest data values for the different fields of application along with the corresponding time period when these data values were received. The visual modification allows a user to easily identify the different time periods when these data values were received. The visual modification also allows integration of the data modification information in the existing application layout without requiring additional screen space to show data values. Further, the user can also view previously received data values for any of the fields without the requirement of scrolling through history information of all the fields of the application.

Figure 2B:
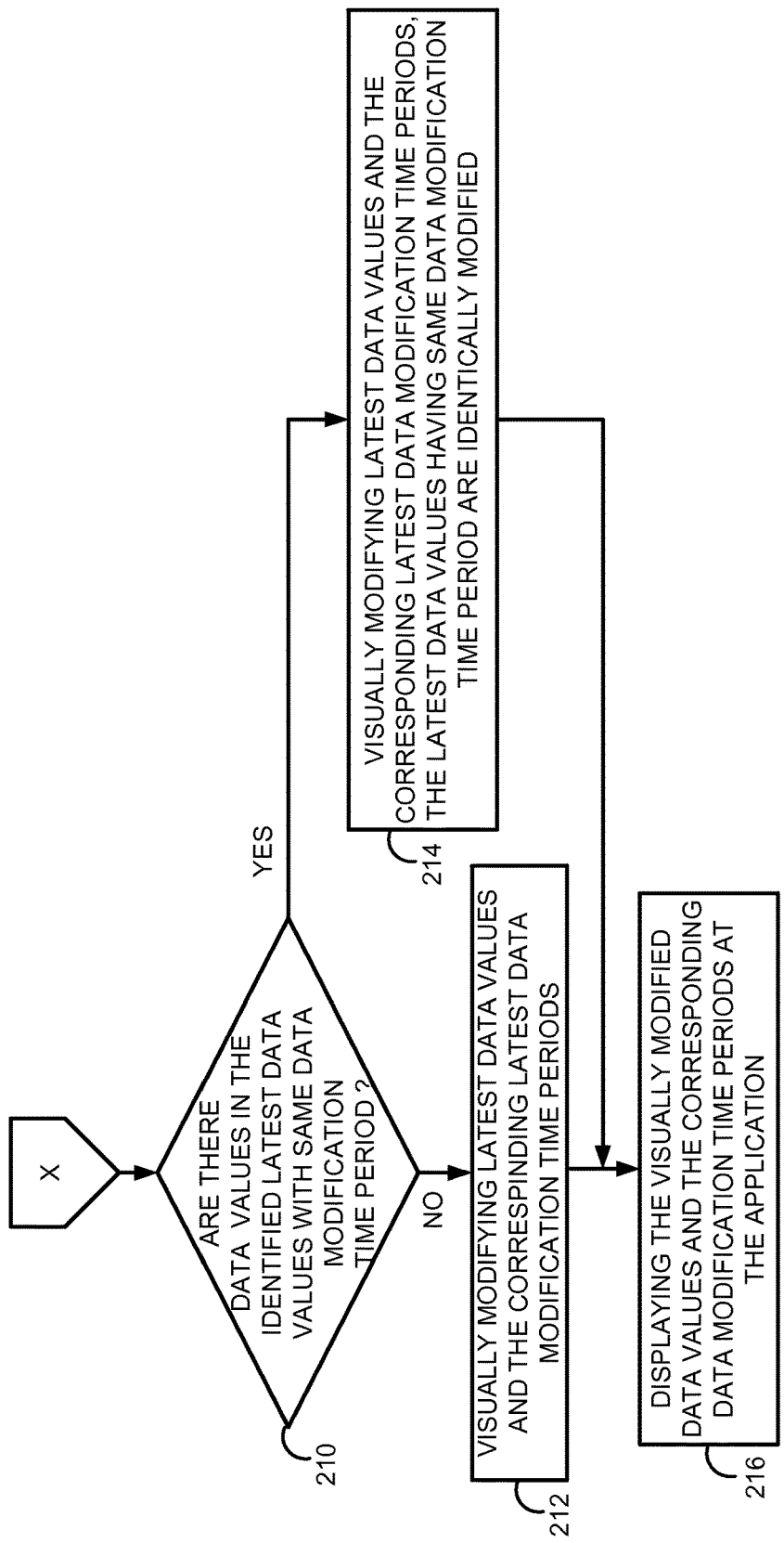

FIGS. 2A-2B are different portions of a flow diagram 200 which illustrates a process to display the latest data values of an application, according to an embodiment. At 202, a request is received to view the latest data modification information for an application. The latest data modification information includes the latest data values for the fields of the application and the corresponding latest data modification time periods when the latest data values are received. In one embodiment, a user viewing the application may request the latest data modification information by clicking a "history" button at the application.

At 204, data values and corresponding data modification time periods are retrieved. The data values may include data received for different fields of the application. The corresponding data modification time period is the time when the data values are received at the application. The data values and the corresponding data modification time periods may be retrieved from a database. In one embodiment, a data value received at the application is persisted at the database along with the data modification time period when the data value is received at the application. Persistence refers to the characteristic of state that outlives the process that created it. Persistence is achieved by storing the state as data in computer data storage. For example, the data values and the corresponding data modification time periods received and persisted for a hotel booking application are shown in Table 3.

TABLE 3

| Room Number | Name | Data Modification Time Period |
|---|---|---|
|  | Ms. Betty | 23 Oct., 2015 |
| 138 | Mr. Michael | 22 Oct., 2015 |
| 137 | Mr. James | 21 Oct., 2015 |

At 206, the latest data modification time periods are identified from the retrieved data modification time periods. The latest data modification time periods may be identified for data values of the different fields of the application. The latest data modification time period is the time when the latest data value of a particular field is received. The latest data modification time period corresponding to a field may be the last time when a data value for the particular data field is received which, in turn, may be received before the request to view the latest data modification information. The latest data values corresponding to the identified latest data modification time periods are then determined at 208. The latest data values corresponding to the different fields of the application may be determined. In this case, the current data values for the different data fields of the application are identified as the latest data values.

For the hotel booking application shown in Table 3, the latest data modification time period ("22 Oct., 2015") for the latest data value for the "Room Number" field is identified. Further the latest data modification time period "23 Oct., 2015" for the "Name" field is also identified. The latest data values "138" ("Room Number" field) and "Ms. Betty" ("Name" field) corresponding to the identified latest data modification time periods 23 Oct., 2015 and 22 Oct., 2015, respectively, are then determined.

At 210, a determination is made whether there are data values in the determined latest data values that have same latest data modification time period. In case there are no latest data values with same latest data modification time period (condition in 210 is no), then the latest data values and the corresponding latest data modification time periods are visually modified at 212. In one embodiment, the latest data value and the corresponding latest data modification time period are identically modified. For the hotel booking application shown in Table 3, the latest Room Number data value "138" and the corresponding latest data modification time period "22 Oct., 2015" may be identically modified such that they both have a green font color, for example. Similarly the latest name data value "Ms. Betty" and the corresponding latest data modification time period "23 Oct., 2015" may be identically modified such that they both have a red font color. Different font colors may be used because each data value corresponds to a different latest data modification time period.

In case there are data values in the determined latest data values with the same latest data modification time period (condition in 210 is yes), then the latest data values and the latest data modification time period are visually modified such that the latest data values having same latest data modification time period are identically modified at 214. In one embodiment, identical modification is a process of applying the same visual modification to different data values. For example, two data values may be identically modified by changing their font color to the same color, changing their font size to the same size, or changing any of their visual characteristics to the same value. For the hotel booking application shown in Table 3, if the latest Room Number data value "138" and the latest name data value "Ms. Betty" are both received on the same date, for example, Oct. 30, 2015, then the latest Room Number data value "138" and the latest name data value "Ms. Betty", and their corresponding data modification dates ("30 Oct., 2015") may be identically modified such that all three data values (one room number, one name, and one date) have the same font color, for example, green.

In one embodiment, other modifications may be applied to the data values to show the latest data modification information in addition to or instead of the visual data modifications described above. For example, the latest data modifications may be represented by sound or any other identifiable differentiator. The visually modified data values and the corresponding data modification time periods are displayed at the application at 216. In one embodiment, the data modification time periods are displayed in a portlet on the user interface displaying the application. Portlets are pluggable user interface software components that are managed and displayed in a web- or enterprise-portal. The visually modified data are displayed at the user interface along with the portlet displaying the data modification time periods. In the hotel booking application shown in Table 4, the latest visually modified name data value "Ms. Betty" and the corresponding visually modified latest data modification time period "23 Oct., 2015" is shown in red color, as represented by italicized text. Similarly, the latest visually modified room number data value "138" and the corresponding visually modified latest data modification time period "22 Oct., 2015" is shown in green color, as represented by bold text.

TABLE 4

| Room Number | Name | Data Modification Time Period |
|---|---|---|
|  | Ms. Betty | 23 Oct., 2015 |
| 138 |  | 22 Oct., 2015 |

Figure 3:
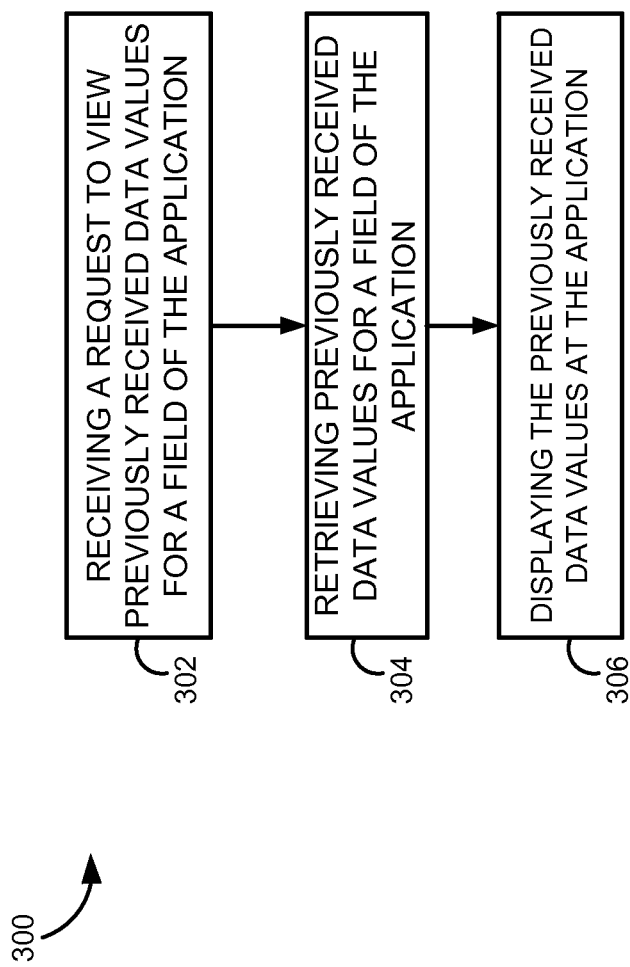
FIG. 3 is a flow diagram illustrating a process to display previously received data values for a field of the application, according to an embodiment.

FIG. 3 is a flow diagram 300 illustrating a process to display previously received data values for a field of the application, according to an embodiment. At 302, a request is received to view previously received data values for a field of the application. In one embodiment, historical data information includes the previously received data values for a particular field, prior to receiving the latest data value. For example, consider a "name" data field in an application that receives a data value "A" on October 21, "B" on October 22, and "C" on October 23. In this case "C" is the latest name data value and the name data values "A" and "B" are previously received data values for the field of the application. A user may request to view previously received data values by placing a pointer, for example, a mouse pointer on an area of the application. The area of the application may include an area that includes the latest data value of the application. The system detects the pointer on the area of the application to receive the request to view previously received data values. In one embodiment, the user places the pointer on the latest data value of the field for requesting to view previously received data values of the field of the application.

At 304, the previously received data values for the field are retrieved. The previously received data values may be retrieved from a database that stores the different data values received at the application. In one embodiment, the retrieved data values, corresponding to the field, may include the latest data value along with the previously received data values for the field. The previously received data values may be identified from the retrieved data values. Finally the retrieved data values are displayed at the application (306). In one embodiment, the retrieved data values may be displayed in a popup adjacent to the latest data value of the field. For example, when a mouse pointer is placed on the latest name data value "C" then a popup including the previous received name data values "A" and "B" may be displayed adjacent to the name data value "C".

FIG. 4 is a screenshot of an exemplary application 400 including visually modified data values, according to an embodiment. The application includes contact information 402 of a particular employee and the data modification time periods 406. All data values having the same data modification period can be modified in the same manner. For example, the data value "Business" 408 corresponding to "E-Mail type" field, the data value "+1-404-665-3421" 410 corresponding to the "Phone Number" field, the data value "Yes" 412 corresponding to the "Is Primary" field, and the data modification time period "04/16/2015" 414 can be displayed in a green color, as represented by a bold font. Similarly, the data value "Business" 416 corresponding to the "Phone type" field", the data value "Yahoo Messenger" 418 corresponding to the "Domain" field, the data value "RevolutionUI@successfactors.com" 420 corresponding to the e-mail address, the data value "www.yahoo.com" 422, and the corresponding data modification time period "04/12/2015" 424 can be shown in a red color, as represented by italicized text. In one embodiment, the previously received data values may also be visually modified and shown at the application. For example, the previously received data values "AOL Instant Messenger" 426, "+1-565-335-8989" 428 , "carla 123" 430 and the corresponding data modification time period "04/09/2015" 432 are visually modified to yellow color, represented by italicized and bold font and displayed at the application.

Figure 5:
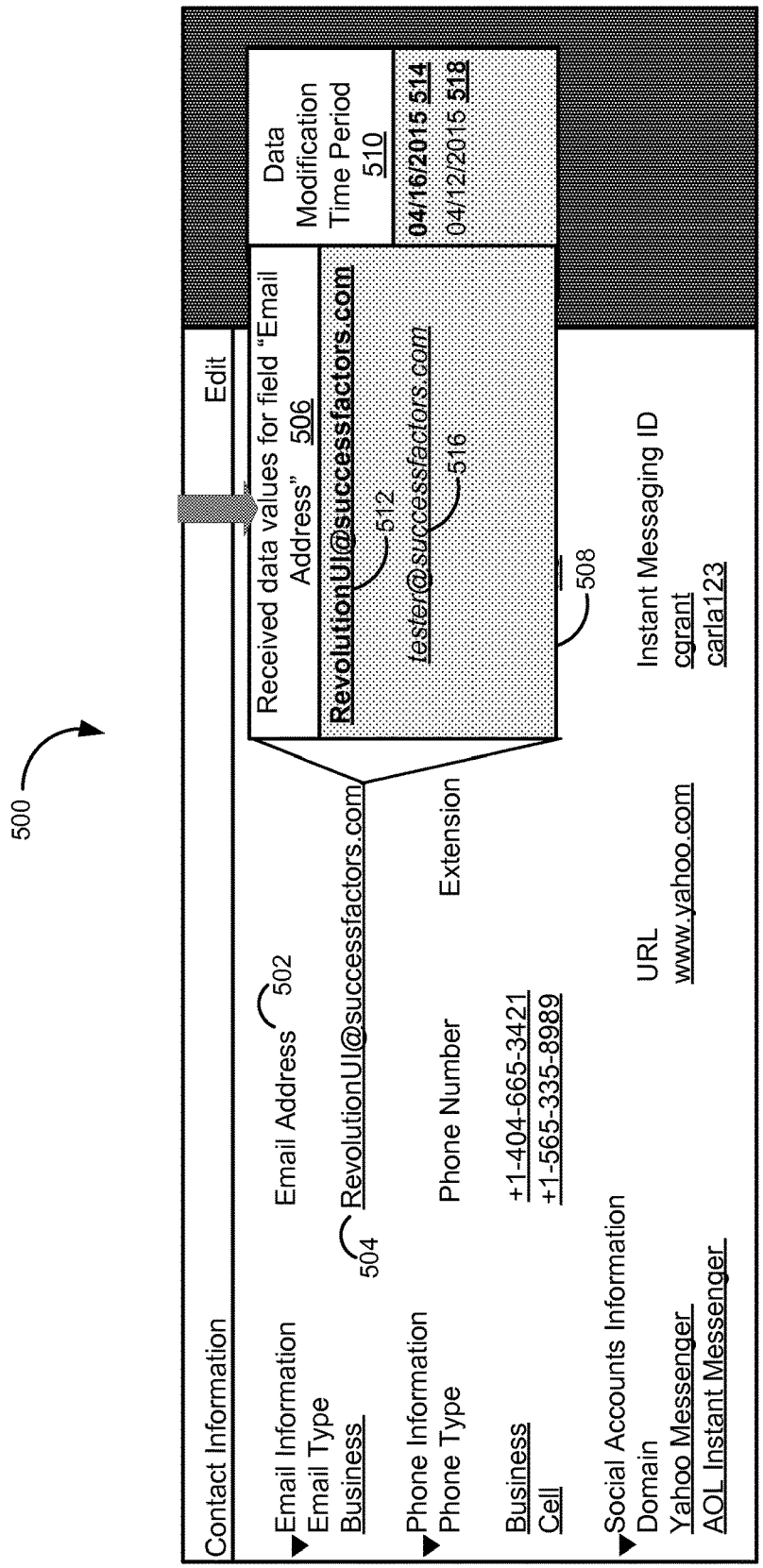
FIG. 5 is a screenshot of an exemplary application including previously received data values for an "E-Mail Address" of the application, according to an embodiment.

FIG. 5 is a screenshot of an exemplary application 500 including previously received data values for an "E-Mail Address" field 502 of the application 500, according to an embodiment. A user sends a request to view previously received data values for the "E-Mail address" field. When a user places a mouse pointer on the latest data value "RevolutionUI@successfactors.com" 504, then the application can display data values 506. Data values 506 can include previously received data values and the latest data value for the "E-Mail" address field, as illustrated in pop-up window 508. In one embodiment, the data values 506 and the corresponding data modification time periods 510 are visually modified to indicate the time period when these data values are received. For example, the latest data value "RevolutionUI@successfactors.com" 512 and the corresponding data modification time period "04/16/2015" 514 when the latest data value is received is shown in green color, as represented by bold text. The previously received data value "tester@successfactors.com" 516 and the corresponding data modification time period "04/12/2015" 518 when this data value is received is shown in red font, as represented by italicized text.

Some embodiments may include the above-described methods being written as one or more software components. These components, and the functionality associated may be used by client, server, distributed, or peer computer systems. These components may be written in a computer language corresponding to one or more programming languages such as, functional, declarative, procedural, object-oriented, lower level languages and the like. They may be linked to other components via various application programming interfaces and then compiled into one complete application for a server or a client. Alternatively, the components maybe implemented in server and client applications. Further, these components may be linked together via various distributed programming protocols. Some example embodiments may include remote procedure calls being used to implement one or more of these components across a distributed programming environment. For example, a logic level may reside on a first computer system that is remotely located from a second computer system containing an interface level (e.g., a graphical user interface). These first and second computer systems can be configured in a server-client, peer-to-peer, or some other configuration. The clients can vary in complexity from mobile and handheld devices, to thin clients and on to thick clients or even other servers.

The above-illustrated software components are tangibly stored on a computer readable storage medium as instructions. The term "computer readable storage medium" should be taken to include a single medium or multiple media that stores one or more sets of instructions. The term "computer readable storage medium" should be taken to include any physical article that is capable of undergoing a set of physical changes to physically store, encode, or otherwise carry a set of instructions for execution by a computer system which causes the computer system to perform any of the methods or process steps described, represented, or illustrated herein. A computer readable storage medium may be a non-transitory computer readable storage medium. Examples of a non-transitory computer readable storage media include, but are not limited to: magnetic media, such as hard disks, floppy disks, and magnetic tape; optical media such as CD-ROMs, DVDs and holographic devices; magneto-optical media; and hardware devices that are specially configured to store and execute, such as application-specific integrated circuits ("ASICs"), programmable logic devices ("PLDs") and ROM and RAM devices. Examples of computer readable instructions include machine code, such as produced by a compiler, and files containing higher-level code that are executed by a computer using an interpreter. For example, an embodiment may be implemented using Java, C++, or other object-oriented programming language and development tools. Another embodiment may be implemented in hard-wired circuitry in place of, or in combination with machine readable software instructions.

Figure 6:
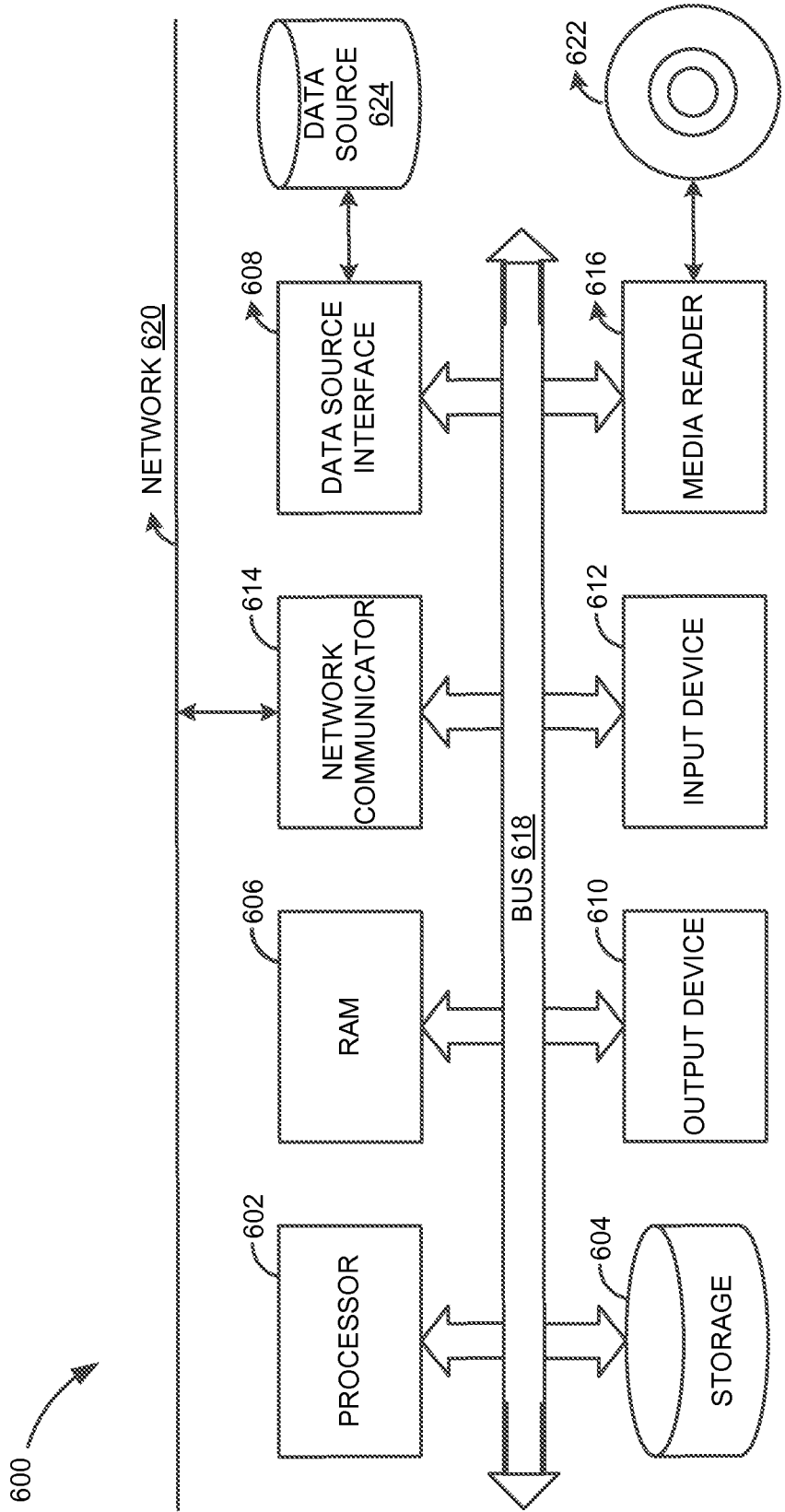
FIG. 6 is a block diagram illustrating a computing environment for visually representing information related to an application, according to an embodiment.

FIG. 6 is a block diagram of an exemplary computer system 600. The computer system 600 includes a processor 602 that executes software instructions or code stored on a computer readable storage medium 622 to perform the processes described above with respect to FIGS. 1-5. The computer system 600 includes a media reader 616 to read the instructions from the computer readable storage medium 622 and store the instructions in storage 604 or in random access memory (RAM) 606. The storage 604 provides a large space for keeping static data where at least some instructions could be stored for later execution. The stored instructions may be further compiled to generate other representations of the instructions and dynamically stored in the RAM 606. The processor 602 reads instructions from the RAM 606 and performs actions as instructed. According to one embodiment, the computer system 600 further includes an output device 610 (e.g., a display) to provide at least some of the results of the execution as output including, but not limited to, visual information to users and an input device 612 to provide a user or another device with means for entering data and/or otherwise interact with the computer system 600. Output devices 610 and input devices 612 could be joined by one or more additional peripherals to further expand the capabilities of the computer system 600. A network communicator 614 may be provided to connect the computer system 600 to a network 620 and in turn to other devices connected to the network 620 including other clients, servers, data stores, and interfaces, for instance. The modules of the computer system 600 are interconnected via a bus 618. Computer system 600 includes a data source interface 608 to access data source 624. The data source 624 can be accessed via one or more abstraction layers implemented in hardware or software. For example, the data source 624 may be accessed by network 620. In some embodiments the data source 624 may be accessed via an abstraction layer, such as, a semantic layer.

A data source is an information resource. Data sources include sources of data that enable data storage and retrieval. Data sources may include databases, such as, relational, transactional, hierarchical, multi-dimensional (e.g., OLAP), object oriented databases, and the like. Further data sources include tabular data (e.g., spreadsheets, delimited text files), data tagged with a markup language (e.g., XML data), transactional data, unstructured data (e.g., text files, screen scrapings), hierarchical data (e.g., data in a file system, XML data), files, a plurality of reports, and any other data source accessible through an established protocol, such as, Open DataBase Connectivity (ODBC), produced by an underlying software system (e.g., ERP system), and the like. Data sources may also include a data source where the data is not tangibly stored or otherwise ephemeral such as data streams, broadcast data, and the like. These data sources can include associated data foundations, semantic layers, management systems, security systems and so on.

In the above description, numerous specific details are set forth to provide a thorough understanding of embodiments. One skilled in the relevant art will recognize, however that the embodiments can be practiced without one or more of the specific details or with other methods, components, techniques, etc. In other instances, well-known operations or structures are not shown or described in details.

Although the processes illustrated and described herein include series of steps, it will be appreciated that the different embodiments are not limited by the illustrated ordering of steps, as some steps may occur in different orders, some concurrently with other steps apart from that shown and described herein. In addition, not all illustrated steps may be required to implement a methodology in accordance with the one or more embodiments. Moreover, it will be appreciated that the processes may be implemented in association with the apparatus and systems illustrated and described herein as well as in association with other systems not illustrated.

The above descriptions and illustrations of embodiments, including what is described in the Abstract, is not intended to be exhaustive or to limit the one or more embodiments to the precise forms disclosed. While specific embodiments of, and examples for, the invention are described herein for illustrative purposes, various equivalent modifications are possible within the scope of the invention, as those skilled in the relevant art will recognize. These modifications can be made in light of the above detailed description. Rather, the scope is to be determined by the following claims, which are to be interpreted in accordance with established doctrines of claim construction.

What is claimed is:

1. A computer implemented method to visually represent information related to an application, the method comprising:
   receiving, by at least one processor, a request to view latest data modification information for an application;
   retrieving, by the at least one processor, a plurality of data values for a plurality of data fields of the application correspondingly associated with a plurality of data modification time periods;
   based on a first latest data modification time period from the plurality of time periods, identifying, by the at least one processor, one or more first latest data values for one or more data fields from the plurality of data fields associated with the first latest data modification time period, and one or more second data values for one or more different data fields from the plurality of data fields associated with a second latest data modification time period, wherein the second latest data modification time period is different from the first latest data modification time period and is a latest modification time period associated with the one or more different data fields from the plurality; and
   providing for displaying at the application, by the at least one processor, the one or more first latest data values and the first latest data modification period with a first visual modification, and the one or more second data values and the second latest data modification time period with a second visual modification different from the first visual modification.

2. The computer implemented method according to claim 1, further comprising:
   visually modifying, by the at least one processor, the one or more first data values and the first latest data modification period with the first visual modification; and
   visually modifying, by the at least one processor, the one or more second data values and the second latest data modification time period with the second visual modification.

3. The computer implemented method according to claim 2, further comprising:
   displaying, by the at least one processor, the visually modified one or more first data values and the visually modified first latest data modification time period with the first visual modification.

4. The computer implemented method according to claim 1, further comprising:
receiving, by the at least one processor, a request to view previously received data values for a field of the application;
retrieving, by the at least one processor, a plurality of previously received data values, corresponding to the field, from the plurality of data values, wherein a value from the previously received data values is associated with a modification time period from the plurality of data modification time periods indicating when an entry of the value is provided for the field at the application; and
displaying, by the at least one processor, the retrieved plurality of previously received data values at the application.

5. The computer implemented method according to claim 4, wherein receiving the request to view historical data comprises:
detecting, by the at least one processor, a pointer on an area of the application including a latest data value corresponding to the field, wherein the latest data values is associated with a latest modification time period for the field, and wherein a latest data values of a different field from the fields is associated with the same latest modification time period; and
based on the detecting, displaying, by the at least one processor, the latest data value associated with the field and the latest data value of the different field both associated with the same latest modification time period, wherein the latest data value associated with the field, the latest data value of the different field, and the same latest modification time period are identically visually modified when displayed at the application.

6. The computer implemented method according to claim 1, further comprising:
receiving, by the at least one processor, the plurality of data values at the plurality of data modification time periods, wherein the plurality of data values are received at the application, wherein one or more of the plurality of data values are associated with a field from the plurality of fields, and wherein two values associated with two different fields from the plurality of fields are associated with a data modification time period from the plurality of data modification time periods; and
storing, by the at least one processor, the plurality of data values and the corresponding plurality of data modification time periods.

7. The computer implemented method according to claim 1, further comprising:
identifying, by the at least one processor, latest data modification time periods from the plurality of time periods, wherein the latest data modification time periods are associated with latest data values from the plurality of data values associated correspondingly with the plurality of data fields, wherein two fields from the plurality of data fields are associated with one latest data modification time period from the plurality of data modification time periods, and wherein a set of the plurality of data values is associated with a field from the plurality of data fields.

8. A non-transitory computer-readable storage medium to store instructions, which when executed by a computer, cause the computer to perform operations comprising:
receive a request to view latest data modification information for an application;
retrieve a plurality of data values for a plurality of data fields of the application correspondingly associated with a plurality of data modification time periods;
based on a first latest data modification time period from the plurality of time periods, identify one or more first latest data values for one or more data fields from the plurality of data fields associated with the first latest data modification time period, and one or more second data values for one or more different data fields from the plurality of data fields associated with a second latest data modification time period, wherein the second latest data modification time period is different from the first latest data modification time period and is a latest modification time period associated with the one or more different data fields from the plurality; and
provide for displaying at the application the one or more first latest data values and the first latest data modification period with a first visual modification, and the one or more second data values and the second latest data modification time period with a second visual modification different from the first visual modification.

9. The non-transitory computer readable storage medium according to claim 8, further comprises instructions which when executed by the computer further causes the computer to:
visually modify the one or more first data values and the first latest data modification period with the first visual modification; and
visually modify the one or more second data values and the second latest data modification time period with the second visual modification.

10. The non-transitory computer readable storage medium according to claim 9, further comprises instructions which when executed by the computer further causes the computer to:
display the visually modified one or more first data values and the visually modified first latest data modification time period with the first visual modification.

11. The non-transitory computer readable storage medium according to claim 8, further comprises instructions which when executed by the computer further causes the computer to:
receive a request to view previously received data values for a field of the application;
retrieve a plurality of previously received data values, corresponding to the field, from the plurality of data values, wherein a value from the previously received data values is associated with a modification time period from the plurality of data modification time periods indicating when an entry of the value is provided for the field at the application; and
display the retrieved plurality of previously received data values at the application.

12. The non-transitory computer readable storage medium according to claim 11, further comprises instructions which when executed by the computer further causes the computer to:
detect a pointer on an area of the application including a latest data value corresponding to the field, wherein the latest data values is associated with a latest modification time period for the field, and wherein a latest data values of a different field from the fields is associated with the same latest modification time period; and
based on the detection, display the latest data value associated with the field and the latest data value of the different field both associated with the same latest modification time period, wherein the latest data value associated with the field, the latest data value of the different field, and the same latest modification time period are identically visually modified when displayed at the application.

13. The non-transitory computer readable storage medium according to claim 8, further comprises instructions which when executed by the computer further causes the computer to:
receive the plurality of data values at the plurality of data modification time periods, wherein the plurality of data values are received at the application, wherein one or more of the plurality of data values are associated with a field from the plurality of fields, and wherein two values associated with two different fields from the plurality of fields are associated with a data modification time period from the plurality of data modification time periods; and
store the plurality of data values and the corresponding plurality of data modification time periods.

14. The non-transitory computer readable storage medium according to claim 8, further comprises instructions which when executed by the computer further causes the computer to:
identify latest data modification time periods from the plurality of time periods, wherein the latest data modification time periods are associated with latest data values from the plurality of data values associated correspondingly with the plurality of data fields, wherein two fields from the plurality of data fields are associated with one latest data modification time period from the plurality of data modification time periods, and wherein a set of the plurality of data values is associated with a field from the plurality of data fields and
determine the plurality of latest data values, from the plurality of data values, corresponding to the identified latest data modification time periods.

15. A computer system to visually represent information related to an application, the computer system comprising:
a processor to execute a program code; and
a memory coupled to the processor, the memory storing the program code comprising instructions to:
receive a request to view latest data modification information for an application;
retrieve a plurality of data values for a plurality of data fields of the application correspondingly associated with a plurality of data modification time periods;
based on a first latest data modification time period from the plurality of time periods, identify one or more first latest data values for one or more data fields from the plurality of data fields associated with the first latest data modification time period, and one or more second data values for one or more different data fields from the plurality of data fields associated with a second latest data modification time period, wherein the second latest data modification time period is different from the first latest data modification time period and is a latest modification time period associated with the one or more different data fields from the plurality; and
provide for displaying at the application the one or more first latest data values and the first latest data modification period with a first visual modification, and the one or more second data values and the second latest data modification time period with a second visual modification different from the first visual modification.

16. The computer system according to claim 15, wherein the program code further comprises instructions to:
visually modify the one or more first data values and the first latest data modification period with the first visual modification; and
visually modify the one or more second data values and the second latest data modification time period with the second visual modification.

17. The computer system according to claim 16, wherein the program code further comprises instructions to:
display the visually modified one or more first data values and the visually modified first latest data modification time period with the first visual modification.

18. The computer system according to claim 15, wherein the program code further comprises instructions to:
receive a request to view previously received data values for a field of the application;
retrieve a plurality of previously received data values, corresponding to the field, from the plurality of data values, wherein a value from the previously received data values is associated with a modification time period from the plurality of data modification time periods indicating when an entry of the value is provided for the field at the application; and
display the retrieved plurality of previously received data values at the application.

19. The computer system according to claim 18, wherein the program code further comprises instructions to:
detect a pointer on an area of the application including a latest data value corresponding to the field, wherein the latest data values is associated with a latest modification time period for the field, and wherein a latest data values of a different field from the fields is associated with the same latest modification time period; and
based on the detection, display the latest data value associated with the field and the latest data value of the different field both associated with the same latest modification time period, wherein the latest data value associated with the field, the latest data value of the different field, and the same latest modification time period are identically visually modified when displayed at the application.

20. The computer system according to claim 15, wherein the program code further comprises instructions to:
receive the plurality of data values at the plurality of data modification time periods, wherein the plurality of data values are received at the application, wherein one or more of the plurality of data values are associated with a field from the plurality of fields, and wherein two values associated with two different fields from the plurality of fields are associated with a data modification time period from the plurality of data modification time periods;
store the plurality of data values and the corresponding plurality of data modification time periods; and
identify latest data modification time periods from the plurality of time periods, wherein the latest data modification time periods are associated with latest data values from the plurality of data values associated correspondingly with the plurality of data fields, wherein two fields from the plurality of data fields are associated with one latest data modification time period from the plurality of data modification time periods, and wherein a set of the plurality of data values is associated with a field from the plurality of data fields.

* * * * *